United States Patent [19]

Allocca

[11] Patent Number: 4,754,759
[45] Date of Patent: Jul. 5, 1988

[54] NEURAL CONDUCTION ACCELERATOR AND METHOD OF APPLICATION

[75] Inventor: John A. Allocca, Oyster Bay, N.Y.

[73] Assignee: Andromeda Research, Inc., Oyster Bay, N.Y.

[21] Appl. No.: 752,353

[22] Filed: Jul. 3, 1985

[51] Int. Cl.[4] .............................................. A61N 1/36
[52] U.S. Cl. ................................................... 128/421
[58] Field of Search ..................... 128/419 R, 421–423

[56] References Cited

U.S. PATENT DOCUMENTS

| | | | |
|---|---|---|---|
| 3,902,502 | 9/1975 | Liss et al. ................................ | 128/422 |
| 4,232,680 | 11/1980 | Hudleson et al. ...................... | 128/422 |
| 4,255,790 | 3/1981 | Hondeghem ........................... | 128/421 |
| 4,256,116 | 3/1981 | Meretsky et al. ...................... | 128/421 |
| 4,453,548 | 6/1984 | Maurer et al. ......................... | 128/421 |
| 4,520,825 | 6/1985 | Thompson et al. .................... | 128/422 |
| 4,582,063 | 4/1986 | Mickiewicz et al. .................. | 128/421 |

Primary Examiner—William E. Kamm
Attorney, Agent, or Firm—Joseph A. Osofsky

[57] ABSTRACT

An apparatus and a method for generating a train of up-and down-and up-staircase shaped electrical pulses whose peak negative amplitude is two-thirds of its peak positive amplitude and whose frequency can be varied between one hertz and one thousand hertz and applying these electrical pulses to the body for the treatment of nerve function and impairment and pain.

7 Claims, 3 Drawing Sheets

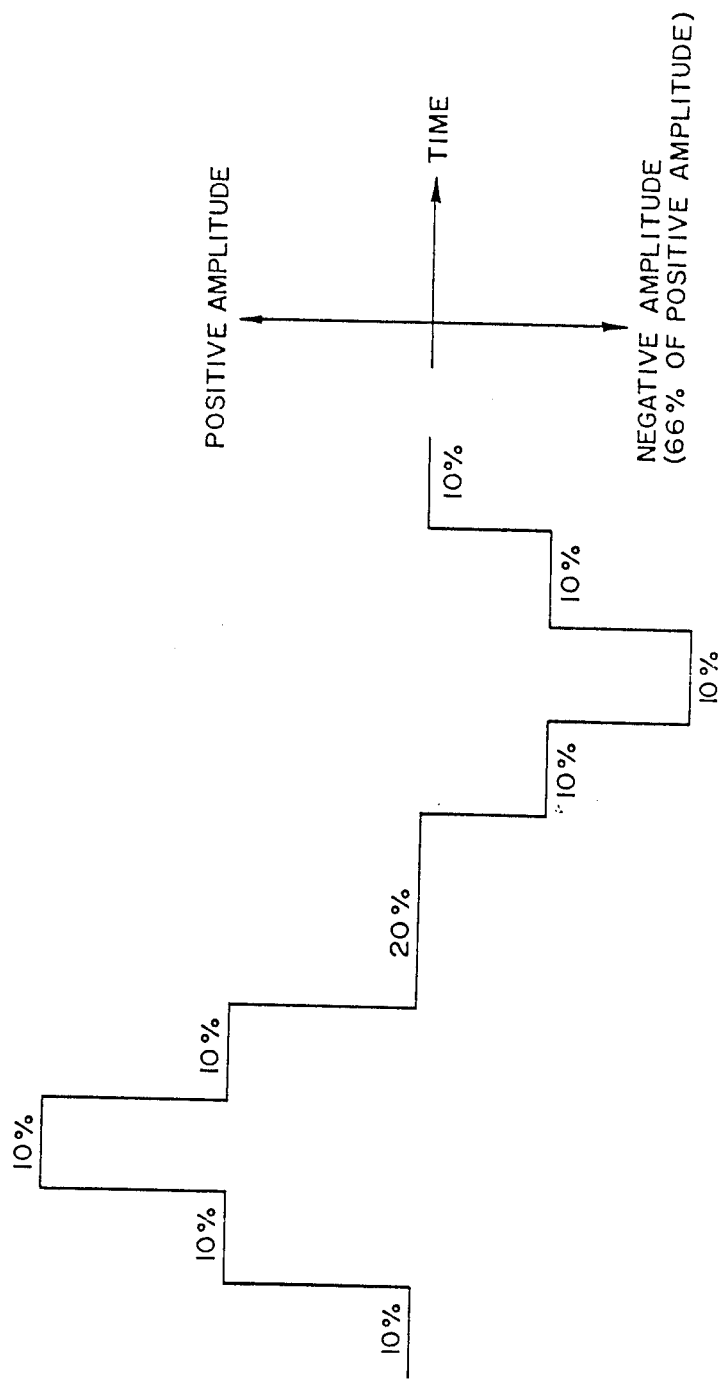

NEURAL CONDUCTION ACCELERATOR AND METHOD OF APPLICATION

BACKGROUND OF THE INVENTION

The present invention concerns a method and apparatus for increasing nerve conduction velocity by the application of uniquely shaped electrical pulses to the nerve system of the human body in order to alleviate nerve disorders caused by disease, physical trauma or chemical trauma. The unique shape of the electrical pulses is derived from a Fourier analysis of nerve biopotentials.

It has been well established that electric stimulation of nerves with low-level electrical pulses (Transcutaneous Electric Neural Stimulation—TENS) is of enormous value for the symptomatic relief of pain. TENS devices have been used primarily for temporary pain relief. Pain and sensory input signals are generated at specific sites in the body and transmitted to the brain through the propagation of ionic conduction in nerves. Pain is sensed in the brain as a result of the propagation of pain signals through the nerves to the brain. If a TENS device is placed between the location of pain and the brain and the electrical signal of the TENS is larger than the pain signal, the brain will sense primarily the TENS signal. This method of pain blocking has been somewhat successful because it decreases the use of drugs, however, the relief of pain for most cases is only temporary. When the TENS device is removed, the pain will reappear if the source of pain has not been changed, similar to the affect of a local anesthetic.

Looking further at the nerve cell, a small excess of negative ions called anions accumulates immediately inside the cell membrane along its inner surface, and an equal amount of positive ions called cations accumulates immediately outside the membrane. The resultant charge or force of these ions produces what is called the membrane potential between the inside and outside of the nerve cell. The membrane potential can change by either an active transport of ions through the membrane, thus creating an imbalance of negative and positive charges on the sides of the membrane or the diffusion of ions through the membrane as a result of ion concentration differences between the two sides of the membrane, which also creates an imbalance of charges. The process of active transport is the moving of ionic molecules against a concentration or pressure gradient. Diffusion is the continual movement of molecules among each other in liquids or gases resulting in a homogeneous distribution or mixing of molecules. Minute quantities of sodium and potassium ions can diffuse through the pores of the cell membrane. If such diffussion should take place over a long period of time, the concentrations of the two ions would eventually become equal inside and outside the cell. This is why the active transport mechanism of sodium(+) and potassium(−) ions, called the sodium-potassium pump is so important. There are several theories of the precise mechanism of this pump, however, for this discussion it suffices to say that the mechanism carrier has the capability of splitting ATP (adenosine triphosphate) molecules and utilizing the resulting energy to transport sodium ions against concentration gradients of 20 to 1 and potassium ions against concentration gradients of 30 to 1. Calcium ions normally decrease the permeability of the membrane to sodium. If sufficient calcium ions are not available, the permeability of the membrane to sodium becomes increased thus increasing the membrane excitability--sometimes so greatly that spontaneous impulses may result and cause neuro-muscular spasm and/or pain. The abrupt changes in membrane potential, which can last a few ten thousandths of a second to a few thousandths of a second, are known as the action potentials, which are the means by which informational signals are transported from one part of the nervous system to another. They can be evoked in a nerve by any mechanism that suddenly increases the permeability of the membrane to sodium ions. This can be caused by electrical stimulation, mechanical compression of the fiber, chemical substances applied to the membrane, or any other event that disturbs the normal resting state (resting potential) of the neural membrane.

The design of TENS devices has been based on the premise that a sufficient amount of charge per unit area must be displaced across the cell membrane in order to raise the transmembrane potential to its firing threshold. Therefore, devices were designed to stimulate nerve cells with single or multiple pulses or spikes of variable width and frequency. Their effectiveness for pain relief varies and is temporary at best; effectiveness is nonexistant for increasing nerve conduction velocity. Poor nerve conduction velocity can result in such manifestations as: sensory deficit, poor neuro-muscular coordination, pain, vasular disorders, etc.

SUMMARY OF THE INVENTION

It is therefore an object of this invention to apply electric pulses, by means of electrodes attached to the body of the patient, which are uniquely shaped to bring about an improvement and/or restoration of impaired neural function.

It is a further object of this invention to provide an apparatus for generating these uniquely shaped electrical pulses at the proper voltage and power levels, and to do so in a manner ensuring the safety of the patient.

The design of the NCA is based on the concept that all bio-potentials (particularly action potentials) must be analyzed through a Fourier analysis, not the standard amplitude/time response. The action potential is the result of many sodium-potassium pumps acting in a single nerve fiber. Although very short in time (1-10 milliseconds), the action potentials must be broken down into even smaller parts thus taking into consideration the specific role and mechanism of sodium-potassium pumps and the regulating calcium channels. One example is that of eyesight. The video signals in the eye are in the frequency range of 2-5 megahertz (2-5 million cycles per second). The optic nerve may have a conduction velocity in the frequency range of 1-10 kilohertz (1-10 thousand cycles per second). Using the standard amplitude/time response one might conclude that the optic nerve is approximately 5000 times too slow to conduct the appropriate video signals. However, the fact is that we can see. The results of analyzing the power spectrum of action potentials, using Fourier analysis, demonstrate the significant level of harmonics on the order of 5-10 megahertz. Therefore, through Fourier analysis a large number of different frequency components of bio-potential's power spectrum can be examined. The NCA is designed to excite nerve cells at different levels for different specified durations and in different vector directions, altering ionic conduction and neurotransmitter diffusion. The specific pulse pattern has been determined as a result of the Fourier analysis of action potentials.

A typical action potential which was so analyzed is the electromyographic action potential of the brachial nerve during flexion. The action potential was obtained by attaching test leads to the arm of the subject and amplifying and processing the resulting electrical signals. The base time of the signal so recorded was approximately one (1) second, corresponding to a base frequency of one (1) hertz. A Fourier analysis of this signal, utilizing standard signal processing equipment and algorithms, yielded a significant power spectrum in the 40 harmonic range. Therefore the specific pulse pattern, generated by the NCA has been designed to have substantially the same harmonic response as the action potential, i.e., a base frequency of approximately one (1) hertz and a significant power spectrum in the 400 harmonic area.

Recent investigations into the role of the calcium interaction of sodium-potassium pumps, indicate a long-term memory effect. If nerves are injured (physically, electrically, chemically, etc.), there appears to be a disruption of calcium in what I refer to as "calcium channels". The disruption may be too little calcium, or too much calcium in inappropriate channels, or any combination thereof. Nerves have been known to recover without the use of external devices. However, this may take months, years or perhaps it may never happen. The NCA performs a very simple task—it reestablishes the proper operation of the calcium channels and the sodium-potassiuim pumps by a specific and complex electrical stimulation which is theoretically similar to the natural process of neural ionic propagation. Once the appropriate neural function has been restored, the NCA may be removed and the condition will remain normal.

This is accomplished by applying, to the body, electrical pulses having the following characteristics. The period of each cycle is adjustable from one second to one millisecond. If T represents the period, the wave form begins at zero amplitude for 0.1T, rises sharply to 50% of its peak positive amplitude which is held for 0.1T, followed by a sharp rise to its peak positive amplitude which is held for 0.1T. Next the output falls sharply to 50% of peak positive amplitude which is held for 0.1T, followed by another sharp drop to zero amplitude which is held for 0.2T. The output then goes sharply negative to 33% of the magnitude of the peak positive value, which is held for 0.1T, followed by a sharp rise of negative polarity to 66% of the peak positive magnitude, which is held for 0.1T. Next the output decreases sharply to 33% of the peak positive magnitude where it is held for 0.1T, followed by a sharp change to zero amplitude where it is held for 0.1T. This waveform, shaped like an up-down-up staircase, is then repeated for the duration of the treatment which can vary from three to fifteen minutes.

It is also an object of this invention to provide an apparatus for carrying out this method of treatment comprising a clock generator, a dual sequential step generator, a differential adder and waveshaper, a low pass filter and voltage and current amplifiers. Controls are provided for adjusting frequency, peak amplitudes and output current levels.

The NCA is powered by rechargeable batteries for maximum safety. Using betteries will eliminate any shock hazard from power lines. For complete safety, the patient cannot be connected to the unit while it is charging. Digital circuitry controls the precise shape and coordination of the complex waveform output. The frequency (rate) is adjustable from 1 hertz to 1000 hertz for different applications. The output amplitude is adjustable to facilitate the precise amount of excitation. Under-excitation will be less effective and over-excitation will cause discomfort. All other parameters have been pre-programmed into the NCA's circuitry for simplicity of operation.

Nerve function is usually impaired because of physical injury to, or pressure on, the nerve. The physical injury or pressure may be removed and the nerve may begin to recover. However, the time period may be months, years or it may never happen. The NCA can play a vital role in speeding up this recovery time. Most patients tested, had complete relief of pain in less than three 15 minute treatments—many after only one treatment. The nervous system (brain and nerves) can control all body functions. The NCA can also be used to control functions through nerves such as: increasing blood flow for greater tissue perfusion and reduction of edema, reduce muscle spasm and inflammation, rehabilitation of nerves and muscles, etc. Pain is usually associated with any or all of the above problems, therefore eliminating the problem which causes the pain, will have a longer or more permanent effect than merely blocking the pain signals.

BRIEF DESCRIPTION OF THE DRAWING

FIG. 3 is an amplitude versus time chart of the output waveform.

DETAILED DESCRIPTION OF THE PREFERRED EMBODIMENT

Figure 1:
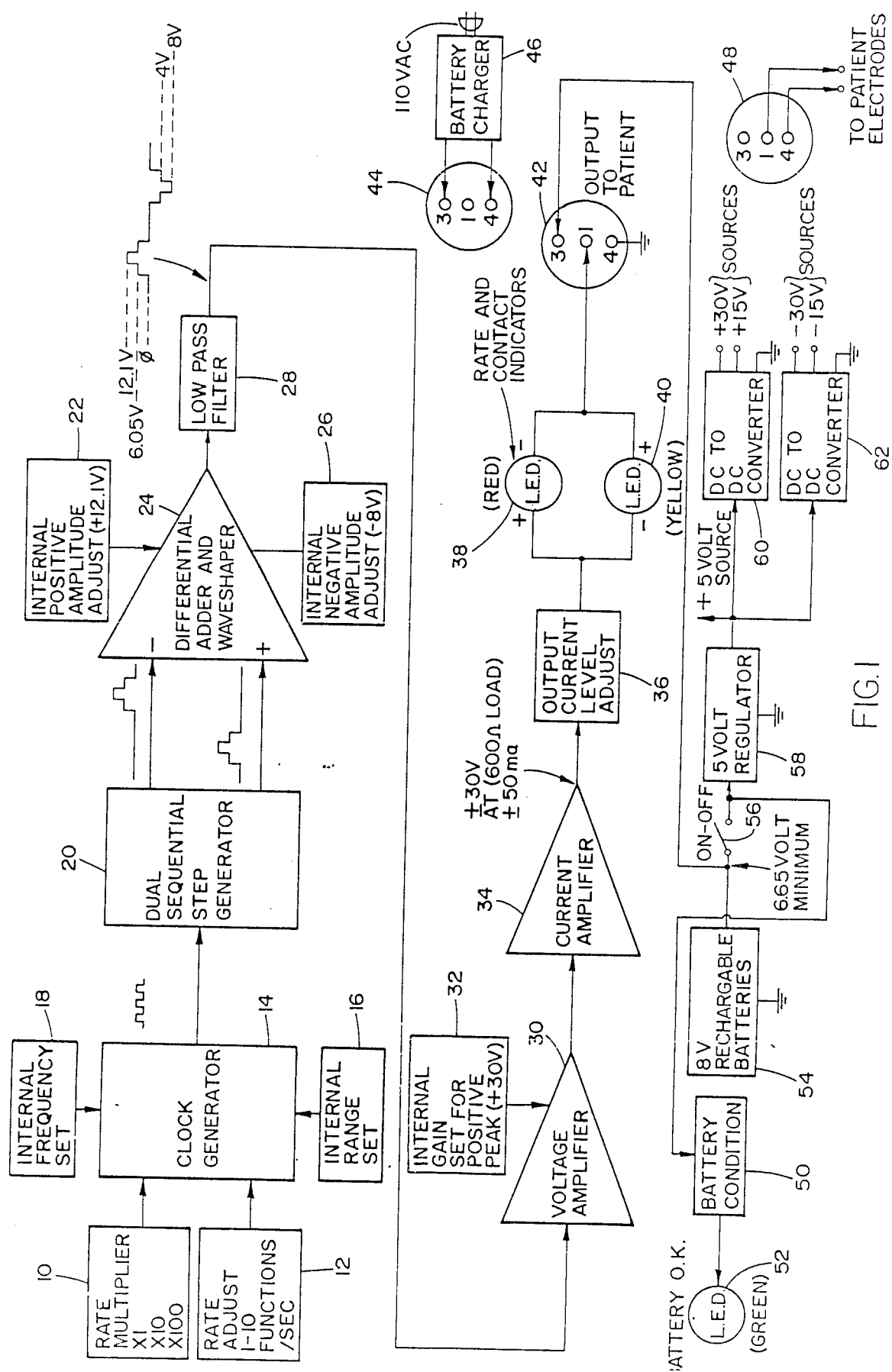
FIG. 1 is a block diagram of a preferred embodiment of the invention.

FIG. 1 shows a block diagram of the Neural Conduction Accelerator. The first stage is a clock generator 14 which generates a continuous train of positive amplitude, rectangular clock pulses varying from 10 hertz to 10,000 hertz. Adjustment is by means of rate multiplier 10 and rate adjustment 12, as well as internal frequency set 18 and range set 16. The clock generator output is connected to a dual sequential step generator 20 which generates two separate, up-and-down staircase shaped, waveforms having positive amplitudes. The two waveforms are inputted to the differential adder and waveshaper 24 which produces the characteristic waveshape shown in FIG. 3. Positive and negative amplitude adjustments, 22 and 26 respectively, are provided for independent adjustment of positive and negative amplitudes. A low pass filter 28 suppresses any spurious oscillations. This is followed by a voltage amplifier 30 and a current amplifier 34. An output current level adjustment 36, indicators 38 and 40 and a plug 42 and mating receptacle 48 to the patient electrodes completes the NCA generator block diagram. Power is supplied by rechargeable batteries 54, voltage regulator 58 and converters 60 and 62. A battery charger 46 is connected to the NCA by means of receptacle 44 which also mates with plug 42. This arrangement effectively prevents use of the NCA with a patient while connected to 110 VAC, thus avoiding any chance of an electric shock due to a malfunctioning battery charger.

Figure 2:
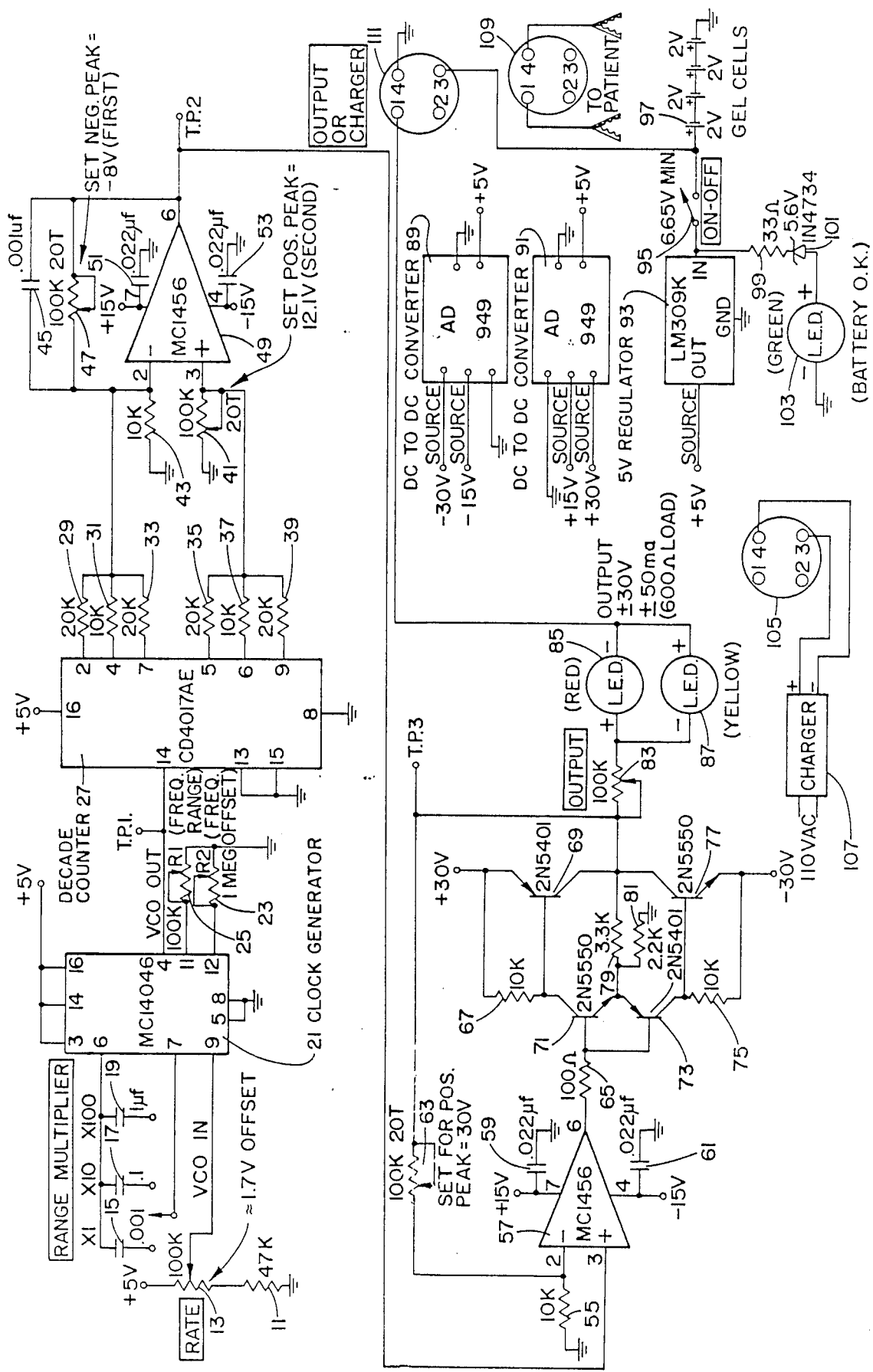
FIG. 2 is a circuit diagram of the preferred embodiment.

FIG. 2 is a circuit schematic diagram of an implementation of the block diagram of the invention shown in FIG. 1.

A clock generator consisting of an astable multivibrator IC (integrated circuit) 21, produces a continuous train of positive amplitude rectangular clock pulses. An input potentiometer 13 acts as a rate control which varies the rate of clock pulses; capacitors 15, 17 and 19 vary the clock rate in multiples of 1, 10, and 100. An internal trimmer potentiometer 23 adjusts the initial frequency offset of the clock.

The clock generator is connected to the dual sequential step generator beginning with decade counter IC 27. Resistors 29, 31 and 33 comprise an adder circuit to form the negative step functions of the generated waveform. Resistors 35, 37 and 39 make up an adder circuit to form the positive step functions of the generated waveform. The IC operational amplifier 49 serves to amplify and set the levels of the previous stage to specific voltages. Internal trimmer potentiometer 47 is used with resistor 43 to set the gain of amplifier 49. Integrating capacitor 45 prevents spurious oscillations of the amplifier 49. Internal trimmer potentiometer 41 is used to set the voltage level of the positive peak of the waveform. Power supply decoupling capacitors 51 and 53 prevent unwanted noise from the power supply. At test point 2 (T.P.2.) the waveform has a positive peak voltage of 12.1 and a negative peak voltage of 8.

Operational amplifier 57 amplifies the voltage and current levels of the previous waveform. Resistor 55 is used in conjunction with internal trimmer potentiometer 63 to adjust the positive voltage level of the waveform to 30 volts. 59 and 61 are power supply decoupling capacitors. 65, 67, 75, 79, and 81 are resistors used in conjunction with transistors 71 and 77 (NPN), and 69 and 73 (PNP), to make up the current amplifier of the stage which has an output current maximum of 50 milliamperes positive and negative.

External output level potentiometer 83 is used to adjust the voltage level of the output. 85 and 87 are front panel light emitting diodes to indicate polarity and the amount of current flowing (by brightness). 111 is the output connector (female) or charger connector. The same connector is used for patient output and battery charging for safety so that a patient cannot be connected to the instrument at the same time it is being charged from the wall socket. 109 is the connector (male) plug and cable which goes to the patient.

DC to DC converters 89 and 91 make up the +15 volts, −15 volt, +30 volt and −30 volt sources. Four 2 volt gel acid batteries 92 are connected in series to form an 8 volt battery supply. The battery supply is regulated to 5 volts by a 5 volt regulator IC 93. Resistor 99, zener diode 101, and light emitting diode 103, make up the battery charge level indicator. 95 is an on-off switch. This switch may be an ordinary switch or a springwound timer switch. An externally wall-mounted regulated 9 volt power supply 107 is connected to connector (male) plug 105 for charging the battery supply.

FIG. 3 shows the characteristic wave shape generated by the invention. The output amplitude is adjustable and can be adjusted for maximum effectiveness without causing discomfort.

The waveshape is that of an up-, down-, up-staircase, precisely defined with regard to the time axis and the amplitude. The wave period is divided into ten equal segments. The first segment has 0 amplitude; the second segment is maintained at one half the maximum positive amplitude, and the third segment is maintained at the maximum positive amplitude. This is followed by a step decrease to one half the maximum positive amplitude which is maintained through the fourth segment, and this is followed by a step decrease to 0 amplitude which is maintained for the next two segments. The seventh segment has a negative amplitude which is 33% of the maximum positive amplitude, and the eighth segment has a negative amplitude which is 66% of the maximum positive amplitude. The ninth is maintained at a negative amplitude equal to 33% of the maximum positive amplitude and the tenth segment marks a return to 0 amplitude, completing the waveshape.

It is understood that it is possible to effect various changes and modifications in the above invention. For instance, there are a number of ways of generating the characteristic waveform disclosed herein, which will be evident to those skilled in the art. Accordingly the true scope of the invention is set forth in the claims which follow.

I claim:

1. A method of treating nerve impairment which comprises the steps of:
   a. producing a series of up-and down-and up-staircase-shaped electrical pulses, each of said pulses having a preset period T, each of said pulses having a peak positive amplitude V in the first half of said period T, and a peak negative amplitude of two-thirds of V in the second half of said period T; and
   b. applying said series of pulses to a part of the body.

2. The method of treating nerve impairment as in claim 1, wherein each of said pulses has a zero amplitude for the first tenth of said period T, a positive amplitude equal to one half of said peak positive amplitude V during the second tenth of said period T, a positive amplitude equal to said peak positive amplitude V during the third tenth of said period T, a positive amplitude equal to one half of said peak positive amplitude V during the fourth tenth of said period T, a zero amplitude during the fifth and sixth tenths of said period T, a negative amplitude equal to one-third of said peak positive amplitude V during the seventh tenth of said period T, a negative amplitude equal to two-thirds of said peak positive amplitude V during the eighth tenth of said period T, a negative amplitude equal to one-third of said peak positive amplitude V during the ninth tenth of said period T, and a zero amplitude during the tenth tenth of said period T.

3. The method of treating nerve impairment as in claim 2, wherein said period T is any value between a minimum of one millisecond and a maximum of one second.

4. The method of treating nerve impairment as in claim 3, wherein said peak positive voltage V is any value between 0 and 30 volts.

5. The method of treating nerve impairment as in claim 4, wherein the magnitude of the output current is any value between 0 and 50 milliamps.

6. An apparatus adapted for treatment of nerve impairment by application, to the body, of electrical pulses which comprises:
   a. clock pulse generator means for generating clock pulses;
   b. dual sequential step generator means for converting said clock pulses into a first and second train of up-and down-staircase shaped pulses phased one-half period apart;

c. differential adder and waveshaper means for combining said first pulse train with inverted said second pulse train to produce a single train of up-and down-and up-staircase shaped pulses;

d. low pass filter means to suppress spurious oscillations in the output of said differential adder and waveshaper means;

e. voltage amplifier means to amplify the voltage output of said low pass filter means; and f. current amplifier means connected to the output of said voltage amplifier means whereby the proper current level is supplied to the body.

7. The apparatus as recited in claim 6 wherein said clock generator means can be adjusted to output clock pulses at any frequency between 10 hertz and 10,000 hertz.

* * * * *